US012558061B2

(12) United States Patent
Lechner et al.

(10) Patent No.: US 12,558,061 B2
(45) Date of Patent: Feb. 24, 2026

(54) SHAPED GEL BODY, METHOD FOR PRODUCING SAME, AND USE THEREOF

(71) Applicant: Johann Lechner, Munich (DE)

(72) Inventors: Johann Lechner, Munich (DE); Bernd Zimmermann, Starnberg (DE); Michael Sturm, Weßling (DE)

(73) Assignee: Johann Lechner, Munich (DE)

( * ) Notice: Subject to any disclaimer, the term of this patent is extended or adjusted under 35 U.S.C. 154(b) by 549 days.

(21) Appl. No.: 17/599,849

(22) PCT Filed: Mar. 3, 2020

(86) PCT No.: PCT/EP2020/058962
§ 371 (c)(1),
(2) Date: Sep. 29, 2021

(87) PCT Pub. No.: WO2020/201216
PCT Pub. Date: Oct. 8, 2020

(65) Prior Publication Data
US 2022/0183658 A1 Jun. 16, 2022

(30) Foreign Application Priority Data

Mar. 29, 2019 (DE) .......................... 102019204522.7

(51) Int. Cl.
*A61B 8/00* (2006.01)
*A61B 8/08* (2006.01)
*A61B 8/12* (2006.01)

(52) U.S. Cl.
CPC .......... *A61B 8/4281* (2013.01); *A61B 8/0875* (2013.01); *A61B 8/12* (2013.01);
(Continued)

(58) Field of Classification Search
CPC ....... A61B 8/4281; A61B 8/0875; A61B 8/12; A61B 8/42; A61B 8/4272; A61B 8/4411; A61B 8/4422; A61B 8/15
See application file for complete search history.

(56) References Cited

U.S. PATENT DOCUMENTS 4,787,070 A * 11/1988 Suzuki ................. A61B 8/4281
601/2
4,966,953 A * 10/1990 Shikinami .............. C08G 18/10
528/66

(Continued)

FOREIGN PATENT DOCUMENTS

DE 68923448 T2 12/1995
DE 202007008008 U1 * 12/2007 ............. A61B 5/682

(Continued)

OTHER PUBLICATIONS

Imbeau, Jacques. "Introduction to through-transmission alveolar ultrasonography (TAU) in dental medicine." CRANIO® 23.2 (2005): 100-112 (Year: 2005).*

(Continued)

*Primary Examiner* — Sean D Mattson
(74) *Attorney, Agent, or Firm* — Kramer & Amado, P.C.

(57) ABSTRACT
A molded gel body used in ultrasonography in the medical or dental field, and the production and use thereof. The molded gel body is used to detect and localize dental cavities in the jawbone by means of through-transmission alveolar ultrasonography (TAU). The molded gel body has a receptacle for receiving an ultrasound transmitter and/or receiver. The molded gel body and the receptacle are adapted to the shape of the ultrasound transmitter and/or receiver. The molded gel body is inserted into a flexible, biocompatible cover which can be filled with an ultrasound gel. To produce the molded gel body, cuboids of a dimensionally stable gel of the appropriate size are preferably cut open over the three (Continued)

of the four lateral sides of the cuboid, but preferably not completely cut through, to produce the receptacle.

7 Claims, 3 Drawing Sheets

(52) U.S. Cl.
CPC .............. *A61B 8/42* (2013.01); *A61B 8/4272* (2013.01); *A61B 8/4411* (2013.01); *A61B 8/4422* (2013.01)

(56) References Cited

U.S. PATENT DOCUMENTS

| | | | | |
|---|---|---|---|---|
| 5,265,614 | A | * | 11/1993 | Hayakawa .............. G10K 11/02 |
| | | | | 600/459 |
| 5,575,291 | A | * | 11/1996 | Hayakawa ............... C08J 3/075 |
| | | | | 600/459 |
| 6,030,221 | A | | 2/2000 | Jones et al. |
| 6,039,694 | A | | 3/2000 | Larson et al. |
| 2004/0068160 | A1 | | 4/2004 | Hascoet et al. |
| 2016/0199027 | A1 | * | 7/2016 | Scully .................. A61B 8/4281 |
| | | | | 424/9.5 |
| 2019/0142555 | A1 | * | 5/2019 | Macoskey ............ A61B 8/4281 |
| | | | | 433/215 |
| 2020/0091393 | A1 | * | 3/2020 | Bae ....................... H01L 33/005 |

FOREIGN PATENT DOCUMENTS

| | | | |
|---|---|---|---|
| DE | 102017011311 | A1 | 6/2019 |
| JP | H02131753 | A | 5/1990 |
| JP | 2005527336 | A | 9/2005 |
| JP | 2017225493 | A | 12/2017 |
| WO | 9001902 | A1 | 3/1990 |
| WO | 2012141672 | A2 | 10/2012 |

OTHER PUBLICATIONS

Notice of Reasons for Rejection issued for JP Patent Application No. 2021-554662 mailed on Sep. 29, 2023.

Bouquot J.E., et al., "Computer-based Thru-transmission Sonography (CTS) Imaging of Ischemic Osteonecrosis of the Jaws—A Preliminary Investigation of 6 Cadaver Jaws and 15 Pain Patients," Oral Surgery, Oral Medicine, Oral Pathology and Oral Radiology Endodontology, 2001, vol. 92, 1 page.

Bouquot J.E., et al., "Neuralgia-Inducing Cavitational Osteonecrosis (NICO), Osteomyelitis in Jawbone samples from Patients with Facial Neuralgia," Oral Surgery, Oral Medicine and Oral Pathology, 1992, vol. 73 (3), pp. 307-319.

First Examination Report for the application No. DE201910204522 dated Oct. 1, 2019, 17 pages.

Imbeau J., "Introduction to Through-Transmission Alveolar Ultrasonography (TAU) in Dental Medicine," The Journal of Craniomandibular Practice, 2005, vol. 2 (23), pp. 100-112.

International Search Report and Written Opinion for International Application No. PCT/E P2020/058962, mailed on May 29, 2020, 25 pages.

Klein M.O., et al., "Ultrasound Transmission Velocity for Non-Invasive Evaluation of Jaw Bone Quality in vivo prior to Dental Implantation," Ultrasound in Medicine & Biology, 2008, vol. 34, pp. 1966-1971.

Langton C. M., et al., "The Measurement of Broadband Ultrasonic Attenuation in Cancellous Bone—A Review of the Science and Technology," IEEE Transactions on Ultrasonic, Ferroelectrics, and Frequency Control, 2008, vol. 7(55), pp. 1546-1554.

Lechner J., "Aseptic-Avascular Osteonecrosis: Local 'Silent Inflammation' in the Jawbone and RANTES/CCL Overexpression," Clinical, Cosmetic and Investigational Dentistry, 2017, vol. 9, pp. 99-109.

Lechner J., et al., "Immune Messengers in Neuralgia Inducing Cavitational Osteonecrosis (NICO) in Jaw Bone and Systemic Interference," European Journey of Integrative Medicine, Elsevier, Amsterdam, NL, Jun. 10, 2010, vol. 2 (2), pp. 71-77.

Lechner J., "RANTES and Fibroblast Growth Factor in Jawbone Cavitation's: Triggers for Systemic Disease," International Journal of General Medicine, 2013, vol. 6, pp. 277-290.

Lechner J., "Validation of Dental X-ray by Cytokine RANTES—Comparison of X-ray findings with Cytokine Overexpression in Jawbone", Clinical, Cosmetic and Investigational Dentistry, 2014, No. 6, pp. 71-79.

* cited by examiner

SHAPED GEL BODY, METHOD FOR PRODUCING SAME, AND USE THEREOF

FIELD OF THE INVENTION

The invention relates to a molded gel body (1), the production thereof and the use thereof in ultrasonography. In particular, the molded gel body is used to detect and localize dental cavities in the jawbone by means of through-transmission alveolar ultrasonography (TAU).

BACKGROUND OF THE INVENTION

In the medical field, pulse-echo sonography is used extensively to visualize all types of soft tissue. In principle, structures inside the body are mapped by evaluating reflections from ultrasonic waves. However, this method is not suitable for obtaining useful information about the condition of the jawbone because of the almost complete reflection of ultrasound at the interface between bone and soft tissue. In particular, the cancellous part of the jawbone cannot be examined with commonly used ultrasound equipment. Therefore, to date, ultrasound has been of very limited use in dentistry.

The condition of the cancellous bone in the jaw can be of great clinical importance. Jeny Bouquot has presented anatomical evidence that the cancellous part of the jaw can be degenerated to a large extent, a phenomenon that he calls, among other things, "ischemic osteonecrosis heading to cavitational lesions." He connects osteonecrosis of the jawbone with neuralgic pain and defines a disease called "neuralgia inducing cavitational osteonecrosis (NICO)"—(cf. J. F. Bouquot. A. A. Roberts, P. Perron and J. Christian, "Neuralgia-inducing cavitational osteonecrosis (NICO). Osteomyelitis in 224 jawbone samples from patients with facial neuralgia," Oral Surg Oral Med Oral Pathol. 1992, 73 (3):307-319; J. Bouquot, W. Martin and G. Wrobleski "Computer-based thru-transmission sonography (CTS) imaging of ischemic osteonecrosis of the jaws—a preliminary investigation of 6 cadaver jaws and 15 pain patients," Oral Surg Oral Med Oral Pathol Oral Radiol Endod. 2001, 92: 550.)

Johann Lechner intensively examined the tissue in such damaged areas, which appears as a lump of fat inside an intact cortex. During an operation, this material is simply spooned out. This tissue is in an ischemic, fatty-degenerate state. Lechner therefore defines the observed changes as "fatty-degenerative osteolysis/osteonecrosis of jawbone (FDOJ)." He showed that these lumps of fat found in the jawbone are extremely biochemically active in that they produce large amounts of certain cytokines, namely RANTES (CCL5) and FGF-2, but also PDGF and MCP-1. The concentration of these cytokines is also increased in a number of systemic diseases, such as cancer, dementia, multiple sclerosis, and arthritis. There is strong evidence, due to sensational clinical improvements following surgical removal of such tissues, that the development and persistence of a variety of systemic diseases are related to fatty-degenerative osteolysis/osteonecrosis of the jawbone. However, in most cases there is no local neuralgic pain (NICO) effect. (cf. J. Lechner and V. von Baehr, "RANTES and fibroblast growth factor 2 in jawbone cavitations: triggers for systemic diseases" International Journal of General Medicine 2013, 6: 277-290; 1. Lechner and W. Mayer "Immune messengers in neuralgia inducing cavitational osteonecrosis (NICO) in jaw bone and systemic interference," Eur. J. Integr. Med. 2010, 2 (2): 71-77.)

In addition, according to a recently published publication, it is plausible that NICO and FDOJ as well as "aseptic ischemic osteonecrosis in the jawbone" (AIOJ), all describe the same pathological condition of the jawbone that is listed under Code M87.0 of the International Statistical Classification of Diseases and Related Health Problems, 10th Version (ICD-10). (cf J. Lechner, S. Schuett and V. von Baehr, "A septic-avascular osteonecrosis: local 'silent inflammation' in the jawbone and RANTES/CCL5 overexpression," Clinical, Cosmetic and Investigational Dentistry 2017:9 99-109.)

In addition, the condition of the cancellous part of the jawbone is of great importance for dental implants and for the success of implantology, according to an earlier publication by Bilal Al-Nawas. (cf. A. O. Klein, K. A. Grotz, B. Manefeld, P. H. Kann and B. Al-Nawas, "Ultrasound transmission velocity for non-invasive evaluation of jaw bone quality in vivo prior to dental implantation," Ultrasound in Medicine & Biology 2008, 34: 1966-1971.)

So, there can be serious health risks associated with fatty-degenerative osteolysis of the jawbone. However, a significant problem here is that a jawbone with fatty-degenerative osteolysis does not give any unusual findings on the X-ray. This applies even if the jawbone is in a largely degenerated state and only has fatty tissue instead of the substantia spongiosa of a healthy cancellous bone (FDOJ). The occurrence and phenomena of AIOJ, FDOJ and NICO remain largely unknown and are even disputed or denied because they cannot be detected in any X-ray examination. (cf. J. Lechner, "Validation of dental X-ray by cytokine RANTES—comparison of X-ray findings with cytokine overexpression in jawbone," Clinical, Cosmetic and Investigational Dentistry 2014, 6: 71-79.) in order to overcome the problem described above, a different approach was necessary. Instead of X-rays or other established medical examination methods, the use of through-transmission alveolar ultrasonography (TAU) was evaluated. Through-transmission ultrasonography is well known in some technical fields, such as the aerospace industry, for examining welds, for example. This examination method is also used in the medical field to determine bone density when diagnosing osteoporosis. (cf. C. M. Langton and C. F. Njeh. "The Measurement of Broadband Ultrasonic Attenuation in Cancellous Bone—A Review of the Science and Technology," IEEE Transactions on Ultrasonics, Ferroelectrics, and Frequency Control, 2008 (55) 7: 1546-1554.)

U.S. Pat. No. 6,030,221 A is likely to be the first disclosure of a device for through-transmission alveolar ultrasonography (TAU) in order to detect cavities in the jawbone. This TAU device generates an ultrasonic pulse and sends that pulse through a patient's jawbone. The ultrasound pulse is then measured and recorded by an ultrasound receiver unit. Attenuations in the amplitude of the ultrasound pulse (damping) indicate pathological changes in the jawbone. The results are presented on a color monitor and show different colors corresponding to different degrees of damping.

The TAU device according to U.S. Pat. No. 6,030,221 A was commercially available for several years. It was the Cavitat Ultrasonograph CAV 4000, developed by engineers at Cavitat Medical Technologies. This known TAU device used a plurality of receiver elements, the frequency of the transmitted ultrasonic pulse and the sound wave being in the range of approximately 2.5 MHz. The received sound waves were processed by a digital converter at an operating frequency of approximately 100 MHz. Jacques Imbeau describes in more detail the underlying principles and the handling of this device in the publication J. Imbeau, "Introduction to Through-Transmission Alveolar Ultrasonography (TAU) in Dental Medicine," The Journal of Craniomandibular Practice, 2005 (23) 2: 100-112.

The aforementioned TAU device has a number of disadvantages, which are explained in more detail by Imbeau, loc. cit., Pp. 106/107. The German patent application DE 10 2017 011 311.4 describes a new TAU device that overcomes these disadvantages. This relates to the difficulty of positioning the ultrasound transmitter and receiver in a reproducible and simple manner, it also relates to the low sensitivity of the old Cavitat device, then the mechanical instability of the ultrasound receiver and finally the inability to calibrate the device.

The reliable acoustic coupling of the measuring device and the object to be measured is critical for all ultrasonography. This coupling is particularly difficult with irregularly shaped objects, such as those in the jaw area. The problem addressed by the present invention is therefore that of compensating different distances between the alveolar ridge and the surfaces of the ultrasound transmitter and/or receiver. In addition, the invention is intended to allow the position of the ultrasound transmitter and/or ultrasound receiver to be adjusted quickly. This is intended to simplify the handling of the molded gel body and make it particularly safe, while further improving the reproducibility of the measurements.

SUMMARY OF THE INVENTION

To solve this problem, the present invention describes a molded gel body, the production thereof and the use thereof in ultrasonography.

The molded gel body is preferably cuboid or is derived from a cuboid and has an interior space, a recess, an incision, slit or the like (hereinafter "receptacle") for receiving an ultrasound transmitter and/or receiver. The edges of the cuboid are preferably chamfered or rounded. At least one of the narrow lateral surfaces can preferably be rounded and/or the edges of the bottom and top surface are curved outward in pairs. The molded gel body and the provided receptacle are preferably adapted to the shape of the ultrasound transmitter and/or receiver. However, any molded initial body can also be provided with a receptacle for receiving an ultrasound transmitter and/or receiver.

For easier handling, the receptacle is filled with sufficient quantities of a non-dimensionally stable ultrasound gel. Furthermore, the molded gel body (or bodies) can be inserted into a flexible, biocompatible protective cover, which can also be filled with a non-dimensionally stable ultrasound gel.

The invention also relates to the system consisting of molded gel bodies, optionally in a flexible, biocompatible protective cover and optionally filled with non-dimensionally stable ultrasound gel, as well as ultrasound transmitters and/or receivers.

To produce the molded gel body, cuboids of a dimensionally stable gel of the appropriate size are cut open over the narrow lateral surfaces of the cuboid, but preferably not completely cut through and only over three of the four sides to produce the receptacle or, if not completely cut open, closed or glued on the edges only over two of the four sides.

The molded gel bodies, optionally in protective covers, are used for medical or dental use, preferably as disposable items and in particular for through-transmission alveolar ultrasonography to localize cavities in the jawbone. The use with a device and for a method according to DE 10 2017 011

311.4 is particularly preferred. Thus, the teaching of DE 10 2017 011 311.4 with regard to the use of molded gel bodies is further developed by the invention.

DETAILED DESCRIPTION OF PREFERRED EMBODIMENTS OF THE INVENTION

Figures 1, 2, 3, 4:
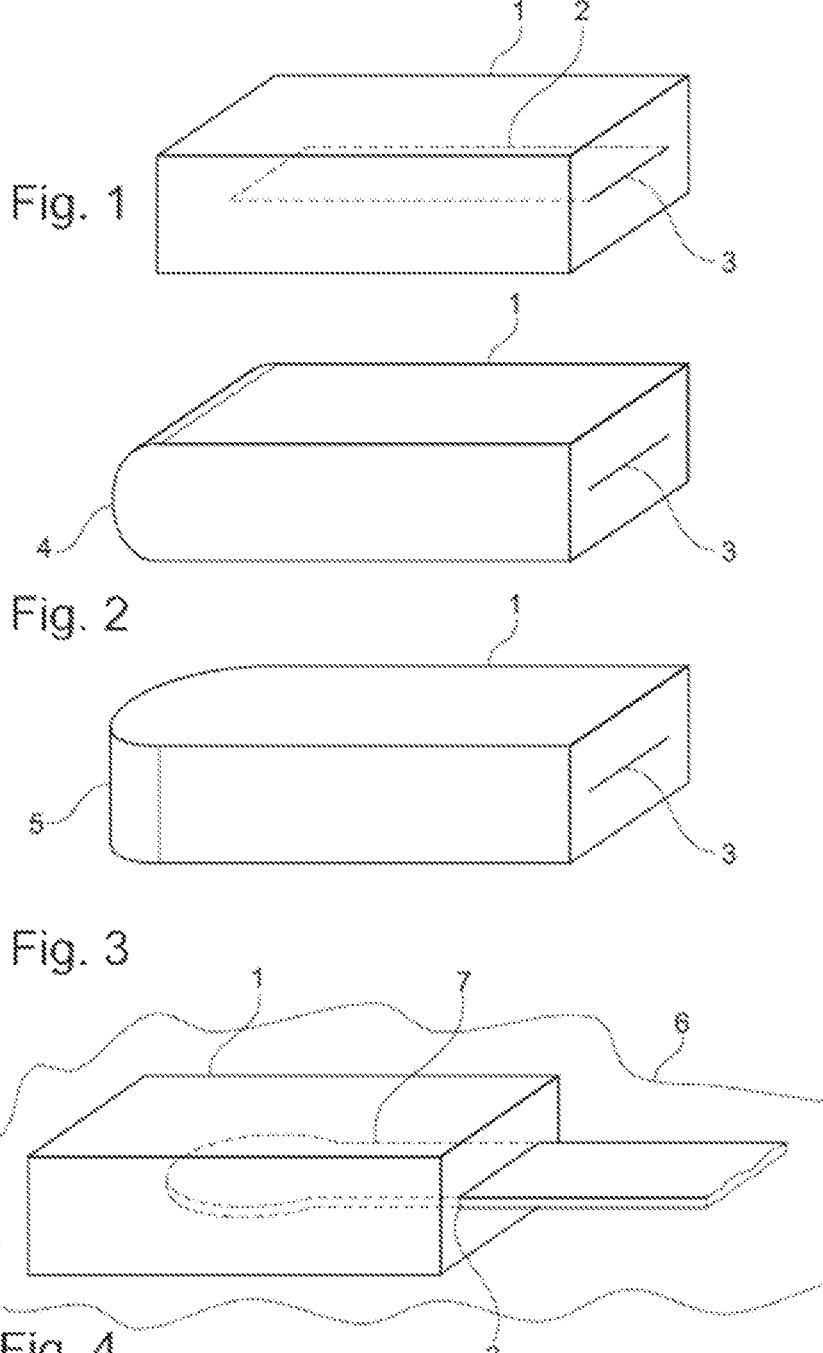
FIG. 1 shows a molded gel body (1) comprising a receptacle (2) according to the invention.
FIG. 2 shows a molded gel body comprising a rounded lateral surface (4)
FIG. 3 shows a molded gel body in which the edges of the bottom and top surface (5) are curved outward in pairs.
FIG. 4 shows a ready-to-use system consisting of a molded gel body (1), a protective cover (6) and an ultrasound transmitter or receiver (7)

FIG. 1 shows a molded gel body (1) for use in ultrasonography, in which the provided receptacle (2) is shown in dashed lines. Due to the elasticity of the molded gel body, the receptacle (2) can be designed as a simple incision or as a slit which is marked on the lateral surface with the reference sign (3); an ultrasound transmitter and/or receiver can simply be pushed through the incision (3) into the receptacle (2). The elastic molded gel body (1) is preferably substantially cuboid and has a bottom and a top surface as well as four narrower lateral surfaces.

Figure 5:
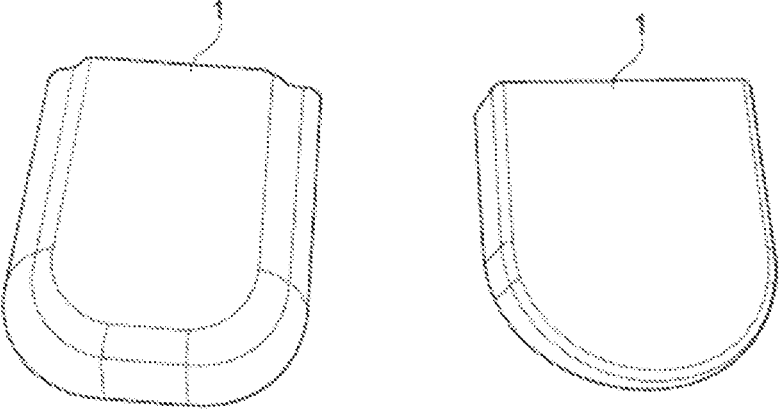
FIG. 5 shows two examples of the molded gel body (1) in which both the narrow lateral surfaces are rounded and the edges of the bottom and top surface are curved outward in pairs.

The molded gel body can also be derived from a cuboid in such a way that at least one of the narrow lateral surfaces is rounded (4), as shown in FIG. 2. An alternative rounded portion (5) is shown in FIG. 3. In particularly preferred embodiments, both rounded shapes are combined, as shown in FIG. 5.

A receptacle (2) is provided inside the molded gel body, which can receive a transmitter and/or receiver (7) provided for the ultrasonography, the receptacle (2) having an opening (3) to the outside in order to be able to insert the transmitter or receiver (7) and to receive connecting elements of the ultrasound transmitter and/or receiver (7).

The molded gel body (1), in particular in the case of a substantially spherical shape, has a diameter between 1 cm and 10 cm, preferably between 1.5 cm and 7 cm, particularly preferably between 2 cm and 5 cm, and/or, in the case of a substantially cuboid shape, has a length of the bottom or top surface of 1 cm to 10 cm, preferably 2 cm to 8 cm and particularly preferably 2.5 cm to 5.0 cm, a width of the bottom or top surface of 1 cm to 8 cm, preferably 1.5 cm to 6.0 cm, particularly preferably 2 cm to 4 cm and very particularly preferably 3.0 cm and/or a height of 0.8 cm to 4 cm, preferably 1 cm to 3 cm and particularly preferably 1.0 cm to 1.4 cm.

Such a molded gel body (1) is simple to produce, safe and easy to use, and provides good acoustic coupling and thus the prerequisite for good measurement results.

The measurement results are improved if the molded gel body (1) does not have any sharp edges and corners. In order to achieve this, the corners and outer edges of the molded gel body (1) are preferably chamfered or rounded.

It is also preferred if the external shape of the molded gel body (1) is adapted to the shape of the ultrasound transmitter and/or receiver (7) to be received. It is also preferred if the provided receptacle (2) is adapted to the shape of the ultrasound transmitter and/or receiver (7) to be received.

For reasons of ultrasound technology, it has proven to be advantageous to dimension the ultrasound transmitter larger than the ultrasound receiver, and therefore the associated molded gel bodies can also be manufactured in different sizes. It is also preferred to make at least one gel layer in the molded gel body provided for an ultrasound transmitter thicker than the gel layers in the molded gel body which is provided for the ultrasound receiver. One possible embodiment provides 7 mm and 4 mm for the thickness of the gel layers that are in the path of the ultrasound.

In the practice of TAU measurements according to DE 10 2017 011 311.4, it has proven to be advantageous to use the ultrasound receiver enorally, i.e., inside the mouth, and to position the ultrasound transmitter on the outside of the patient's cheek and, optionally, to establish good acoustic coupling using some ultrasound gel. In the case of difficult anatomical conditions inside the mouth, however, it is possible that the ultrasound receiver only delivers good measurement results in a single position. Under certain circumstances, however, this can mean that the ultrasound transmitter no longer allows sufficient acoustic coupling, unless a thicker gel layer is provided for the ultrasound transmitter—as taught here—which accordingly can be more strongly deformed than is possible with thin gel layers without losing the acoustic coupling.

When taking measurements in the jaw area, it is advantageous that the ultrasound transmitters and receivers (7) for their part do not have any sharp corners and edges, in order to avoid discomfort or pain when used on the patient. Therefore, the outer shape of the ultrasonic measuring elements is preferably rounded, as shown in FIG. 4. This means that the provided receptacle (2)—preferably in the region opposite the opening (3)—is also rounded. Furthermore, it is preferred that a rounded (4) lateral surface opposes the opening (3) and/or that the edges of the bottom and top surface are curved outward in pairs (5) and face the opening (3).

In the pulse-echo sonography in the prior art, for example, a gel layer, a so-called front section, must be used over bones or joints for reasons of sound technology. Such a gel layer can be provided in a simple manner by using a molded gel body (1) for an ultrasound head of any shape, which molded gel body has a receptacle (2) inside for the ultrasound head, which receptacle is surrounded by a gel layer the thickness of which is 1.0 cm to 5.0 cm, preferably 1.2 cm to 3 cm.

When selecting suitable dimensionally stable, elastic gels, one can start from thermoplastic elastomers in which a polymeric main body can receive a suitable low-molecular-weight liquid. Care must be taken that the acoustic properties of the molded gel bodies do not adversely affect the measurements. This means that the molded gel body preferably comprises a dimensionally stable elastic gel, which has a sound velocity in the range from 1,460 m/s to 1,615 m/s and a sound attenuation in the range from 0.3 dB/cm to 1.5 dB/cm (1 MHz).

Suitable dimensionally stable elastic gels should be soft, (very) elastic and (very) flexible, so that the most complete possible contact of the dimensionally stable elastic gel with the ultrasound receiver and the alveolar ridge can always be ensured. It has been shown that all of these properties are fulfilled at least when the gel used has a recovery speed for spontaneous recovery of at most 80 mm/sec.

Because of the flexibility of the gel, it is also possible to adjust the position of the measuring unit, consisting of the ultrasound transmitter and receiver, without disturbing the contact of the gel and without disturbing the measurements. The dimensionally stable property of the gel prevents the gel from starting to flow before or during the measurement and disappearing into regions in which measurements are not taken. This happens easily when using non-dimensionally stable, commonly used ultrasound gels and means that reliable measurements often cannot be carried out.

The dimensional stability of the molded gel body (1) is particularly important for ultrasonography in the upper jaw, because in the upper jaw area the tendency for ultrasound gels to flow away is very pronounced due to gravity. Using the molded gel bodies (1) according to the invention, however, TAU measurements can also be carried out easily and reproducibly in the upper jaw area without the need for further auxiliary constructions to hold the gel in place.

Dimensionally stable elastic gels with the properties mentioned are commercially available, for example SONOGEL Sonokit soft, article numbers 6510 and 6520, which are sold by Sonogel Vertriebs-GmbH in Bad Camberg, Germany. It is a styrene block copolymer with a hydrogenated central block made of styrene-ethylene/butylene-styrene or styrene-ethylene/propylene-styrene and belongs to the class of thermoplastic elastomers, with paraffin oil as a low molecular weight component. Other suitable materials are, for example, silicones mixed with silicone oils or very plasticized polyvinyl chloride.

In order to facilitate the insertion of the ultrasound transmitter and/or receiver (7) into the molded gel body (1), it has proven useful to fill the provided receptacle (2) with a non-dimensionally stable gel (hereinafter referred to as "ultrasound gel") routinely used in ultrasonography. The amount of ultrasound gel required for this depends on the viscosity of the ultrasound gel and the restoring forces of the molded gel body (1).

Furthermore, for reasons of hygiene and application, it is advantageous to provide the molded gel body (1) with a flexible protective cover (6) that is as biocompatible as possible. FIG. 4 shows a ready-to-use system consisting of a molded gel body (1), a protective cover (6) and an ultrasound transmitter or receiver (7) and the opening of the receptacle (2) to the outside (3). The non-dimensionally stable ultrasound gel is not shown. The system also includes the arrangement—likewise not shown—in which both the ultrasound transmitter and the ultrasound receiver are inserted into the molded gel body (with or without a protective cover).

With the protective cover, the transport and handling of the molded gel bodies are made much easier. It is also possible to fill this protective cover (6) with an ultrasound gel, the molded gel body (1) being completely or partially surrounded by the ultrasound gel, depending on the amount of ultrasound gel used. The protective cover (6) can, for example, be made of polyurethane, polyethylene, or latex, but preferably consists of polypropylene.

This results in very simple handling of the molded gel body (1), because in a dental practice only the ultrasound transmitter and/or receiver (7), for example, have to be inserted into the molded gel body (1), which is located in the protective cover (6), which insertion can be done cleanly, conveniently, and quickly due to the ultrasound gel already being filled in. The use of gloves also makes it easy to meet hygiene requirements, and measurements in the oral cavity can be carried out without any further precautions.

Figures 6, 7:
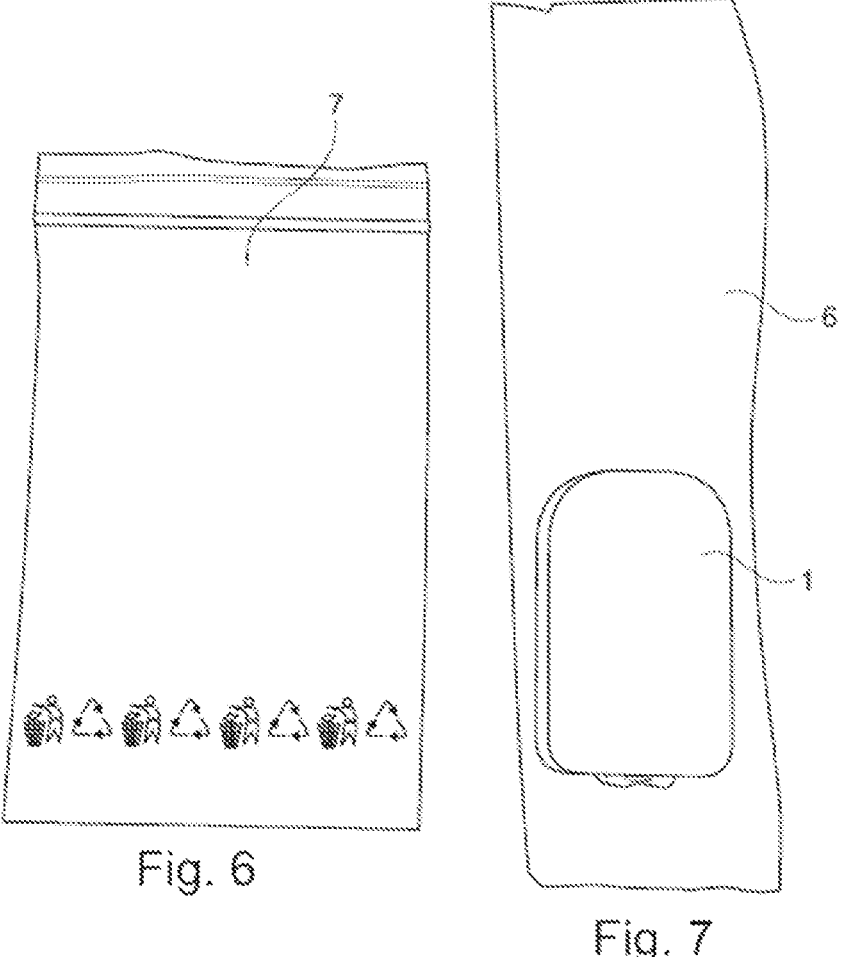
FIG. 6 shows a true-to-scale plastic bag for transporting the molded gel body (1) in a protective cover (6) according to FIG. 7.
FIG. 7 shows a true-to-scale, ready-to-use molded gel body (1) in a protective cover (6).

FIG. 7 shows, true-to-scale, the ready-to-use molded gel body (1) in a protective cover (6) next to a true-to-scale plastic bag for transport in FIG. 6.

The critical absence of air bubbles in the molded gel body (1) is already checked during production and is therefore part of the quality control during the production of the molded gel body. The molded gel bodies (1) used are therefore free from air bubbles. If air bubbles appear when filling the ultrasound gel, these air bubbles can easily be recognized and they can be easily removed from the measuring area by gently stroking them with a finger. Using this procedure, no ultrasound gel is inserted into the oral cavity because it is not tolerable for toxicological and legal reasons, but above all it would be uncomfortable and unreasonable for the patient.

The invention also relates to a system, which consists of an ultrasound transmitter and/or receiver (7), inserted into the particular elastic molded gel body (1). The molded gel body (or bodies) can in turn be located in a protective cover (6) which is flexible, as biocompatible as possible, and can be filled with an ultrasound gel. A system comprising an ultrasound transmitter and receiver (7), molded gel bodies (1) and protective covers (6), filled with ultrasound gel, is immediately suitable and prepared for the intended measurements.

The invention also relates to a method for producing a molded gel body (1), in which a molded body is cut open and only partially glued again in order to form the receptacle (2) of the molded gel body (1).

This method is based on a molded body made of a dimensionally stable elastic gel. A cuboid or a molded body derived from a cuboid—with bottom, top and lateral surfaces and associated outer edges—is preferably completely or partially cut open between the bottom and top surface in order to form the receptacle (2) in the molded gel body (1). The cutting can be done with a sharp knife or scissors.

When the molded body is completely cut open, the receptacle (2) inside the molded gel body (1) is formed in that the two halves formed by cutting are placed on top of one another in such a way that the original shape of the molded body is reproduced, and in that the molded body is closed again by each edge on three sides by gluing, so that the remaining receptacle (2) inside has the desired size and the required opening (3) in the receptacle (2) to the outside is ensured.

The molded body, which is only partially cut open, is closed again by the edges on two sides by gluing, so that the receptacle (2) inside the molded gel body (1) has the desired size, and the required opening (3) in the receptacle to the outside is ensured. After gluing, the original shape is restored without further measures, because the molded body was not completely cut open.

For gluing, the surfaces can be heated and made adhesive by contact with a heated metal surface or with a stream of hot air that can be controlled as precisely as possible; the actual gluing takes place by pressing the heated surfaces together. No adhesive is therefore required for gluing, but rather the thermoplastic properties of the polymeric main body used are used for gluing.

It is preferred that the corners and outer edges of the formed molded gel body (1) are at least partially chamfered or rounded using cutting tools in order to create favorable acoustic conditions. Optionally, at least one of the narrow lateral surfaces is also rounded (4), again using cutting tools. The edges of the bottom and top surface can also be curved outward in pairs (5) so that the associated narrow lateral surface appears curved. This shape is also achieved using cutting tools.

Another method for producing the molded gel body (1) according to the invention is based on a dimensionally stable elastic gel having the properties mentioned listed below:

the molded gel body (1) provided for the ultrasound transmitter is larger than the gel body which is provided for the ultrasound receiver (7), and the length, width and/or height of the molded gel bodies differ from one another by a factor of 1.1 to 6, preferably by a factor of 1.2 to 4 and particularly preferably by a factor of 1.5 to 3.

A polymeric main body and a suitable low-molecular-weight liquid are produced by injection molding into a mold with the desired shape as a molded gel body (1) which is removed from the mold after cooling. The receptacle (2) is created in this case by appropriately molded elements of the injection mold.

In the molded gel body (1), the inside of the receptacle (2) can be filled with a non-dimensionally stable ultrasound gel. This makes it easier to introduce the ultrasound transmitter and receiver into the molded gel body (1).

In addition, the molded gel body (1) can be inserted into a flexible, biocompatible protective cover (6), as a result of which the molded gel body can be handled comfortably.

The protective cover (6) can be filled with a non-dimensionally stable ultrasound gel in such a way that the molded gel body (1) inside the cover (6) is completely or partially surrounded by the ultrasound gel. The protective cover (6) should be long enough that the molded gel body (1) and the ultrasound gel can be safely received in the protective cover (6) and cannot accidentally slip out or flow out. When using the device described in DE 10 2017 011 311.4, the length of the protective cover (6) corresponds at least to the length of the two rigid arms, which are parts of the handle described there.

If an ultrasound transmitter and an ultrasound receiver (7) are each inserted into a corresponding molded gel body (1), which is located in a protective cover (6) filled with ultrasound gel, an ultrasound measuring unit is obtained that can be used directly for TAU measurements. Air bubbles in the ultrasound gel only have to be removed from the measuring region by gently stroking them with your finger.

The invention finally relates to the use of a molded gel body (1) for use in ultrasonography, characterized in that the molded gel body (1) is elastic, in that a receptacle (2) for a transmitter and/or receiver (7) is provided inside the molded gel body, and in that the receptacle (2) has an opening (3) to the outside by means of which the ultrasound transmitter and/or receiver (7) can be inserted into the receptacle (2). The invention also relates to a system comprising a molded gel body (1) and an ultrasound transmitter or receiver (7), and optionally an ultrasound receiver. The system is used for ultrasonography in the medical field (e.g., on joints such as the knee) or dental field (in particular in the oral cavity). The invention also relates to the use of a molded gel body (1) according to the invention as a disposable article in the medical or dental field. The invention greatly simplifies the use of the front sections compared to pulse-echo sonography in the prior art.

The molded gel body (1) according to the invention is preferably used in through-transmission alveolar ultrasonography as disclosed herein, and a system as disclosed herein for localizing cavities in the jawbone, particularly preferably in a device and a method according to DE 10 2017 011 311.4.

The use of a molded gel body (1) as disclosed herein and a system as disclosed herein as a disposable article takes place for reasons of hygiene and measurement technology. If the molded gel bodies (1) are replaced by fresh molded gel bodies after each patient, optimal hygiene is ensured. In addition, it is prevented as far as possible that damage inside the molded gel bodies that cannot be seen from the outside can falsify the measurements. Such damage can result from too many consecutive measurements. By changing the molded gel bodies after each patient, however, the probability of such damage occurring is kept negligibly small.

What is claimed is:

1. A method for producing a molded gel body for use in ultrasonography, characterized in that the molded gel body is elastic, in that a receptacle for an ultrasound transmitter and/or receiver is provided inside the molded gel body, and in that the receptacle has an opening to an outside by means of which the ultrasound transmitter and/or receiver can be inserted into the receptacle, wherein the molded gel body is suitable for ultrasonic measurements in a medical or dental field and for insertion into an oral cavity of a patient to detect and localize dental cavities in a jawbone by transmission alveolar ultrasonic measurements, TAU, wherein the method comprises:

(i) preparing an initial molded body consisting of a dimensionally stable, elastic gel, where the initial molded body has a bottom surface, a top surface, and opposed lateral surfaces;

(ii) completely or partially cutting the initial molded body open to produce two cut surfaces extending between the opposed lateral surfaces; and (iii) gluing the two cut surfaces together at the opposed lateral surfaces in such a way that the molded gel body comprising the receptacle and the opening is created.

2. The method according to claim 1 for producing the molded gel body, wherein gluing the two cut surfaces together comprises:

heating the two cut surfaces with a heated metal surface or with a controllable hot air stream; and subsequently pressing said two cut surfaces together.

3. The method according to claim 1 for producing the molded gel body, characterized in that existing corners and/or outer edges are at least partially chamfered or rounded.

4. The method according to claim 1 for producing the molded gel body, characterized in that a lateral surface opposite the opening has a rounded portion, wherein a shape of the rounded portion is already predefined in the initial molded body or is formed subsequently by trimming the lateral surface.

5. The method according to claim 1 for producing the molded gel body, further characterized in that the receptacle inside the molded gel body is filled with a non-dimensionally stable ultrasound gel.

6. The method according to claim 1 for producing the molded gel body, further characterized in that the molded gel body is inserted into a flexible, optionally biocompatible, protective cover.

7. The method according to claim 6 for producing the molded gel body, further characterized in that the protective cover is filled with a non-dimensionally stable ultrasound gel in such a way that the molded gel body inside the cover is completely or partially surrounded by the non-dimensionally stable ultrasound gel.

* * * * *